US008764445B1

(12) United States Patent
DeLuca

(10) Patent No.: US 8,764,445 B1
(45) Date of Patent: Jul. 1, 2014

(54) DENTAL APPLIANCE

(76) Inventor: Helena DeLuca, Parkland, FL (US)

(*) Notice: Subject to any disclaimer, the term of this patent is extended or adjusted under 35 U.S.C. 154(b) by 0 days.

(21) Appl. No.: 13/209,705

(22) Filed: Aug. 15, 2011

Related U.S. Application Data

(60) Provisional application No. 61/374,104, filed on Aug. 16, 2010, provisional application No. 61/434,985, filed on Jan. 21, 2011.

(51) Int. Cl.
A61C 13/10 (2006.01)

(52) U.S. Cl.
USPC .......................................... 433/173; 433/191

(58) Field of Classification Search
USPC ................ 433/191–195, 171–176, 167
See application file for complete search history.

(56) References Cited

U.S. PATENT DOCUMENTS

| 318,581 | A | * | 5/1885 | Sheffield | 433/183 |
|---|---|---|---|---|---|
| 3,091,032 | A | * | 5/1963 | Hirshhorn | 433/182 |
| 3,216,111 | A | * | 11/1965 | Sink | 433/177 |
| 3,656,236 | A | * | 4/1972 | Kurer | 433/221 |
| 3,660,899 | A | * | 5/1972 | Linkow | 433/176 |
| 3,748,739 | A | * | 7/1973 | Thibert | 433/173 |
| 4,193,194 | A | * | 3/1980 | Dalise | 433/177 |
| 4,204,321 | A | * | 5/1980 | Scott | 433/177 |
| 4,445,861 | A | * | 5/1984 | Klepacki | 433/181 |
| 4,514,173 | A | * | 4/1985 | Re | 433/173 |
| 4,657,510 | A | * | 4/1987 | Gittleman | 433/173 |
| 4,661,068 | A | * | 4/1987 | Harrison et al. | 433/181 |
| 4,681,542 | A | * | 7/1987 | Baum | 433/172 |
| 4,693,686 | A | * | 9/1987 | Sendax | 433/173 |
| 4,741,698 | A | * | 5/1988 | Andrews | 433/173 |
| 4,764,115 | A | * | 8/1988 | Willits et al. | 433/177 |
| 5,203,700 | A | * | 4/1993 | Chmel | 433/169 |
| 5,234,341 | A | * | 8/1993 | Johansen | 433/172 |
| 5,324,198 | A | * | 6/1994 | Hazen | 433/171 |
| 5,413,480 | A | * | 5/1995 | Musikant et al. | 433/173 |
| 5,427,906 | A | * | 6/1995 | Hansen | 433/173 |
| 5,451,498 | A | * | 9/1995 | Hazen | 433/171 |
| 5,458,489 | A | * | 10/1995 | Tennyson | 433/181 |
| 5,716,214 | A | * | 2/1998 | Lund et al. | 433/173 |
| 5,803,737 | A | * | 9/1998 | Lyalin | 433/223 |
| 5,873,721 | A | * | 2/1999 | Willoughby | 433/173 |
| 5,885,077 | A | * | 3/1999 | Jeffer | 433/168.1 |
| 5,971,760 | A | * | 10/1999 | Letcher | 433/223 |
| 6,048,203 | A | * | 4/2000 | Rosenberg | 433/173 |
| 6,056,546 | A | * | 5/2000 | Van Handel | 433/169 |
| 6,116,070 | A | * | 9/2000 | Oshida et al. | 72/60 |
| 6,267,596 | B1 | * | 7/2001 | Kalfas | 433/178 |
| 6,299,447 | B1 | * | 10/2001 | Zuest et al. | 433/172 |
| 6,447,296 | B2 | * | 9/2002 | Worthington | 433/183 |
| 6,506,052 | B1 | * | 1/2003 | Hoffman | 433/181 |
| 6,863,530 | B2 | * | 3/2005 | McDevitt | 433/173 |
| 7,108,511 | B1 | * | 9/2006 | Shatkin | 433/174 |
| 7,234,940 | B2 | * | 6/2007 | Weissman | 433/168.1 |
| 7,758,346 | B1 | * | 7/2010 | Letcher | 433/214 |
| 7,785,108 | B2 | * | 8/2010 | Tache et al. | 433/173 |
| 2001/0036618 | A1 | * | 11/2001 | Worthington | 433/183 |
| 2004/0014007 | A1 | * | 1/2004 | Lee et al. | 433/181 |

(Continued)

Primary Examiner — Hao D Mai
(74) Attorney, Agent, or Firm — Gold & Rizvi, P.A.; H. John Rizvi

(57) ABSTRACT

An exemplary dental appliance for application to a jaw of a dental patient includes a teeth section having at least one tooth receptacle, at least one removable retention component carried by the teeth section and at least one fixed retention component adapted for attachment to the jaw of the dental patient and engaged by the at least one removable retention component.

22 Claims, 11 Drawing Sheets

(56) References Cited

U.S. PATENT DOCUMENTS

| | | | |
|---|---|---|---|
| 2004/0086831 A1* | 5/2004 | Lai | 433/183 |
| 2007/0172434 A1* | 7/2007 | Jernberg et al. | 424/49 |
| 2008/0090207 A1* | 4/2008 | Rubbert | 433/171 |
| 2008/0171305 A1* | 7/2008 | Sonenfeld et al. | 433/215 |
| 2010/0086895 A1* | 4/2010 | Randall | 433/172 |
| 2011/0207084 A1 | 8/2011 | Kaigler, Sr. | |
| 2011/0311941 A1 | 12/2011 | Yi et al. | |

* cited by examiner

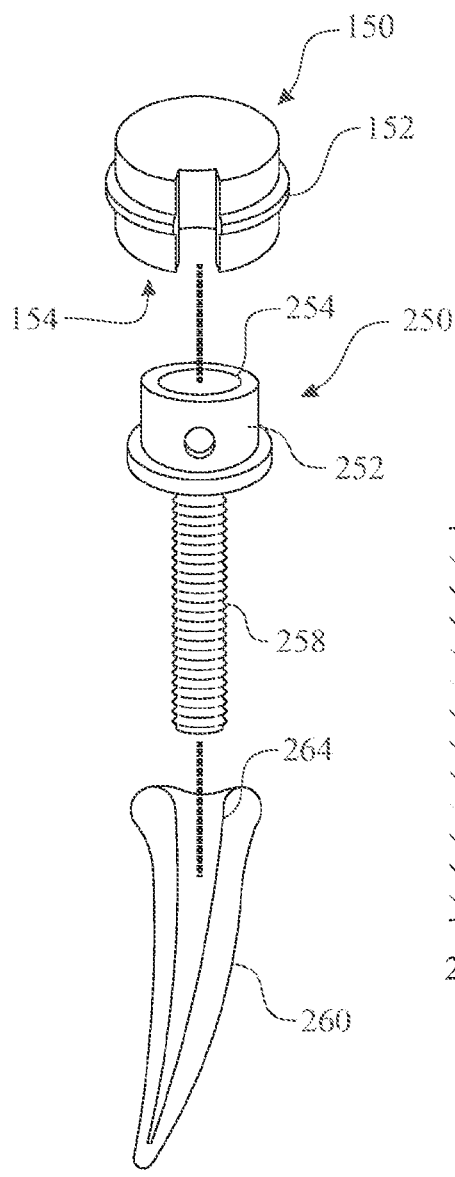
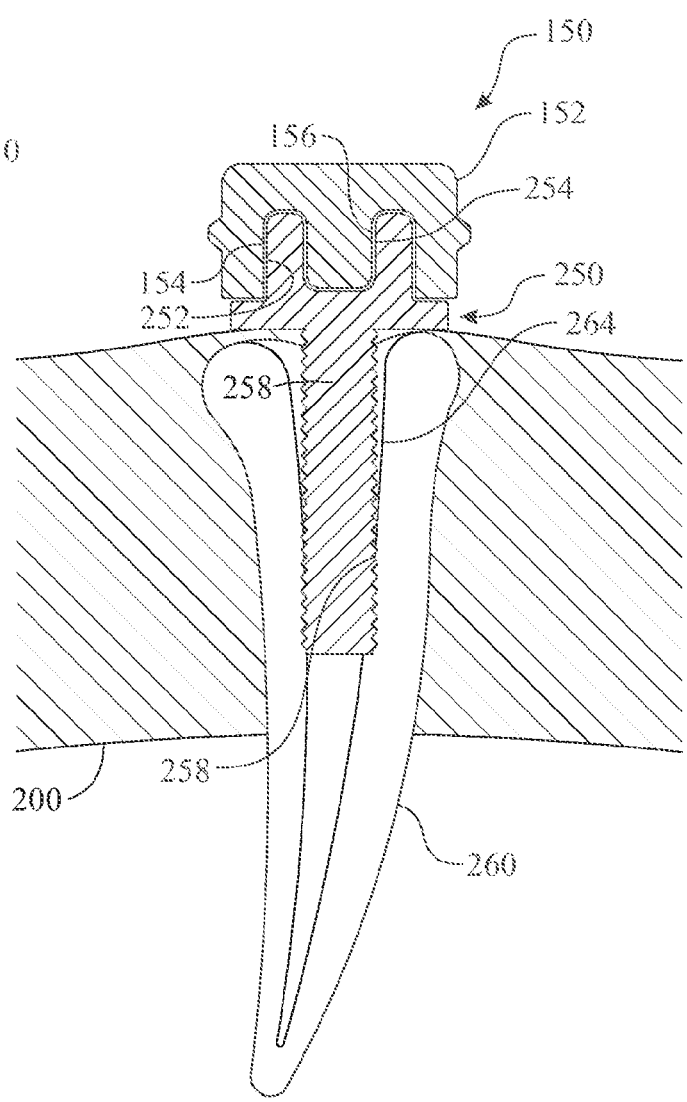
*FIG. 7*  *FIG. 8*

DENTAL APPLIANCE

RELATED US PATENT APPLICATION

This Application claims the benefit of provisional application No. 61/374,104, filed Aug. 16, 2010, and provisional application Ser. No. 61/434,985, filed Jan. 21, 2011, each of which provisional applications is incorporated by reference herein in its entirety.

FIELD OF THE INVENTION

The present invention relates generally to the field of dentistry and more particularly, to a dental appliance which can easily be comfortably applied to improve the smile and function of a patient having an incomplete arch/set of teeth.

BACKGROUND OF THE INVENTION

Dental prosthetics include crowns, dentures, bridgework and veneers which can be used to improve a patient's appearance. Additionally, a dental prosthesis should be engineered to support the utility of the patient's natural teeth. Partial dentures are designed to cosmetically and functionally replace a portion of a patient's upper or lower teeth.

Many patients have problems wearing conventional removable partial dentures. Existing partials can be clumsy and thick and typically cover the upper palate. These characteristics of partial dentures are often a daily source of discomfort and inconvenience for patients.

Implants are generally used for both aesthetic and functional purposes. However, a complete arch of implants is expensive and can be financially out of reach for many patients. While less financially straining than implants, crowns are an option for a single tooth. Porcelain veneers are directed more towards aesthetics and less towards function. Like implants, crowns can be financially limiting for many patients.

Therefore, a dental appliance which cosmetically improves a patient's smile while functionally replacing one or more of the patient's missing teeth without the cost, procedures, and discomfort associated with more extensive dental procedures is needed.

SUMMARY OF THE INVENTION

The present disclosure is generally directed to a dental appliance, the dental appliance comprising:

a continuous wall having an internal surface that engages facial and lingual surfaces of any remaining patient's teeth and an external surface that provides a desired visual impression including a selected color and a selected contour;

an outer surface comprising a tongue side arch and a visible cheek side arch, each of the arches extending from a first posterior location to an anterior portion and then to a second posterior location; and a plurality of retentive points for securing the dental appliance to at least one of the patient's remaining teeth, the retentive points being supra-gingival; and at least one over-denture attachment for securing the dental appliance to an anchor member, wherein the at least one over-denture attachment is located proximate a position respective to a patient's one or more clinically missing teeth and in registration with the at least one over-denture attachment.

The appliance improves the aesthetics of a patient's smile using the patient's existing teeth as the retentive feature, while additionally offering a source for retention in situations in which the patient has few or no existing teeth. This retention function may be accomplished by providing an engaging interface. The engaging interface may be provided by over-denture attachments commonly used in dentistry. The use of such an appliance fabricated to replace missing teeth in an arch, even several adjacent teeth, may utilize conventional over-denture retentive snaps, independent of the particular attachment system chosen by the clinician. The appliance may be fabricated in an all tooth-colored material or may be modified to simulate gingival tissue (i.e. colored/stained to imitate gingival/gum tissue).

The purpose is to provide an alternative treatment option for patients other than that of a conventional removable partial. This option provides the chance for the patient to undergo tooth/teeth replacement that provides both improved function as well as improved aesthetics. The existing use of a variation of this Patent is to provide aesthetics by snapping the appliance over the natural anatomy of existing tooth structure. This variation will achieve retention in regions where the patient no longer has any natural anatomy of existing tooth structure, more specifically in locations in which teeth are absent. The appliance is independent of the number of implants and/or retained roots for retention, in any given area of the mouth, whereby each implant or root provides a source of retention for an appliance for replacement of missing teeth. The number and locations of the retentive features needed, as well as the type of attachment system used, may be determined by the clinician providing the service. It is understood that these considerations would be determined on a case-by-case basis.

The patient may easily insert and remove the removable appliance, enabling the patient to use the appliance as desired. The appliance is designed to replace missing teeth, thereby providing additional function for the patient. In addition, the appliance can include a veneer appearance for existing teeth, thus improving the aesthetics of the patient's existing teeth. The appliance can provide changes to the patient's smile by presenting whiter and re-shaped teeth, as desired.

In another aspect, the dental appliance may include a complete set of teeth colored and shaped to compliment the mouth of a patient.

In another aspect, the dental appliance may include a partial series of teeth colored and shaped to compliment the patient's existing teeth.

In another aspect, the appliance may attach to a tooth root with a possible Locator (Zest) or ERA attachment, or any other attachment system that serves the same purpose of retention.

In another aspect, the appliance may attach to an implant with a possible Locator or ERA attachment, or any other attachment system that serves the same purpose of retention.

In another aspect, the attachment system may further comprise a magnetically attracting connection, an undercut designed abutment connection or a friction-fit connection.

These and other features, aspects, and advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which:

FIG. 7 presents an exploded isometric assembly view of an exemplary root-based appliance retention system;

FIG. 8 presents an assembled sectioned elevation view of the root-based appliance retention system introduced in FIG. 7, wherein a male component snaps into a female component;

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
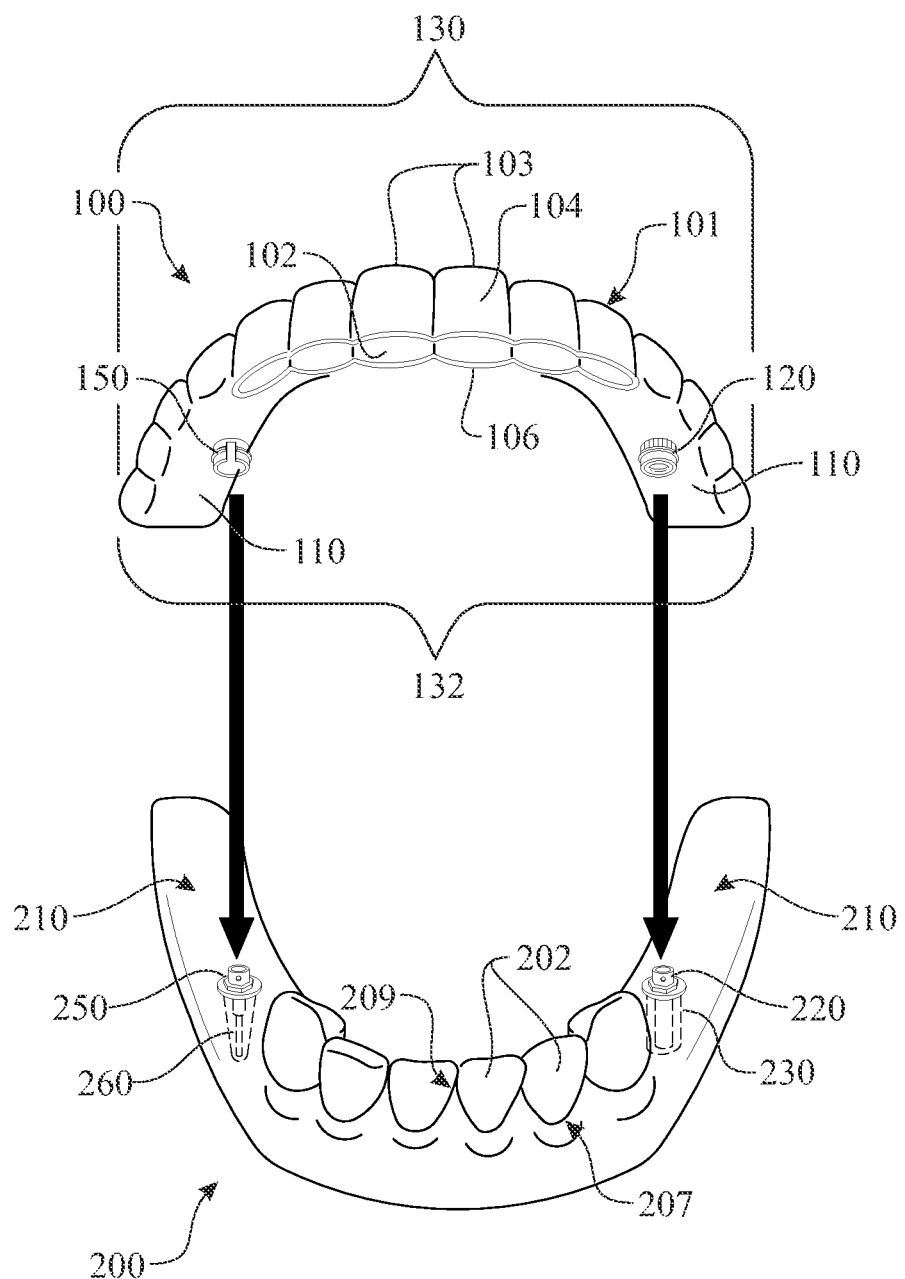
FIG. 1 presents a front assembly elevation view of an exemplary dental appliance (rotated slightly upward) shown in registration with a patient's prepared lower arch just prior to attachment.
Figure 2:
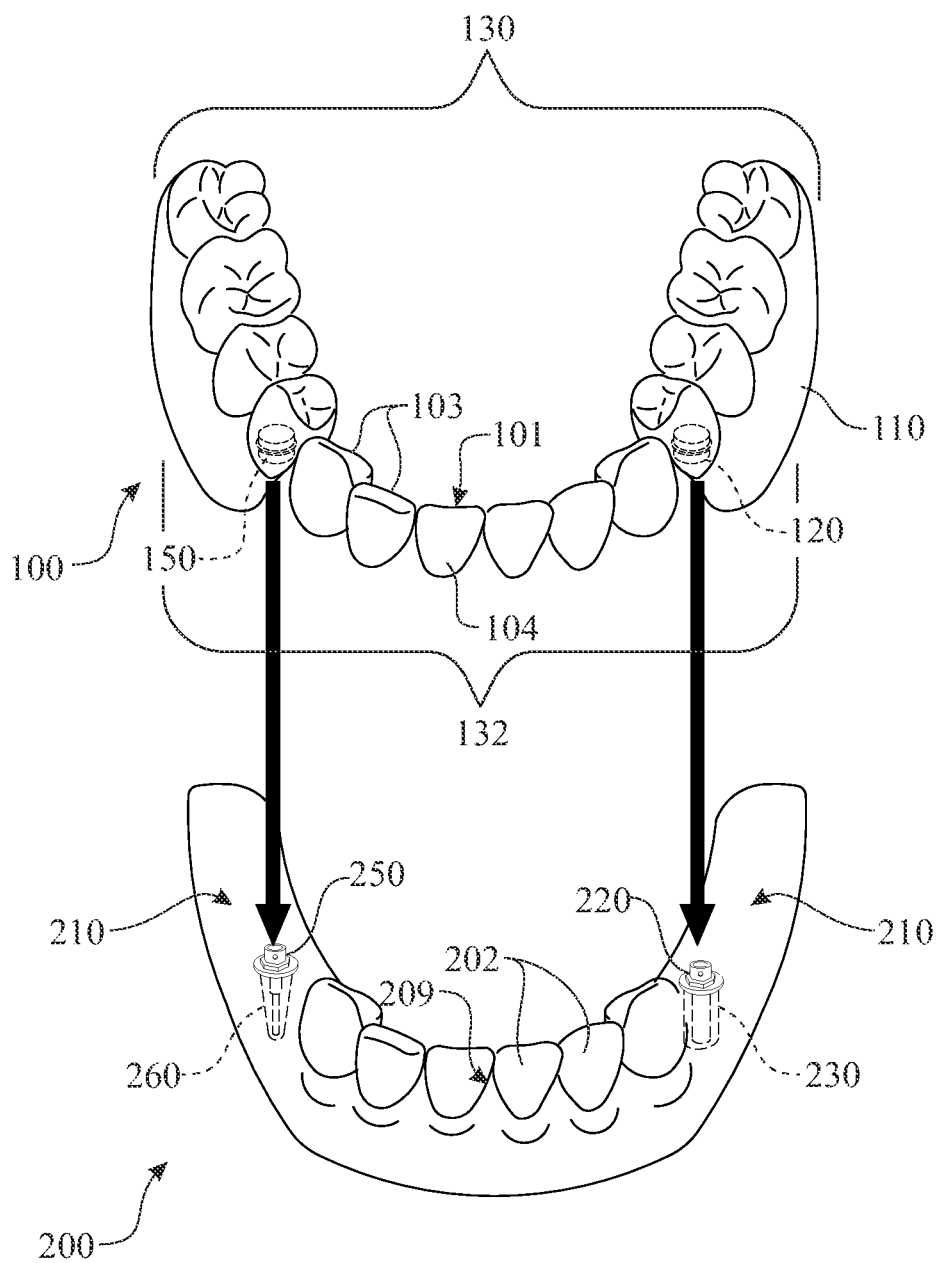
FIG. 2 presents a front assembly elevation view of the exemplary dental appliance introduced in FIG. 1, (rotated slightly downward) shown in registration with the patient's prepared lower arch just prior to attachment.

Referring initially to FIGS. 1-4 and 10-15 of the drawings, an exemplary embodiment of a dental appliance which can be used to aesthetically and functionally improve a patient's dentition is generally indicated by reference numeral 100. In some embodiments, the dental appliance 100 may be configured for placement on a patient's lower dentition, as illustrated in FIGS. 1 and 2. In other embodiments, the dental appliance 100 may be configured for placement on a patient's upper dentition, as illustrated in FIGS. 12-15. In either application, the dental appliance 100 is comfortable to the patient, improves the appearance of the patient's smile and imparts functionality to healthy natural teeth and edentulous (missing teeth) areas of the patient's mouth. In upper dentition applications, the shape of the dental appliance 100 need not cover the patient's palate, thus maintaining the feel and function of the palate. This expedient can be an improvement over conventional dental appliances which may require covering of the palate with a plastic or metal structure or component for retention of the appliance on the patient's dentition.

Figure 3:
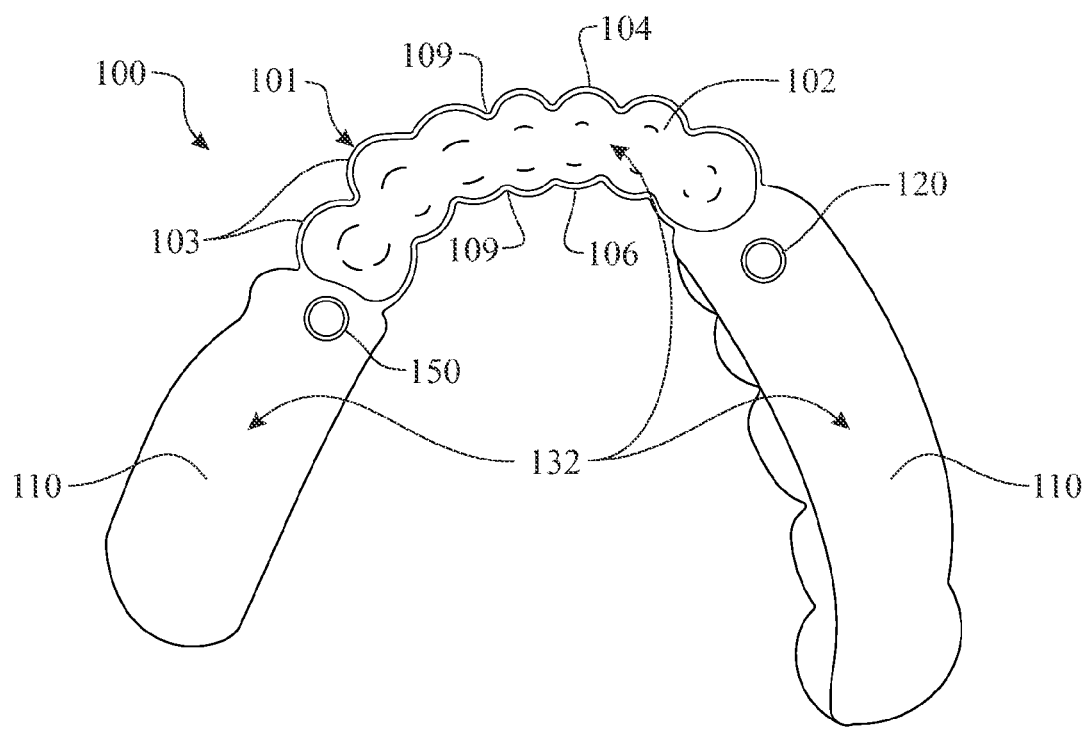
FIG. 3 presents a bottom or under view of a prototype of the exemplary dental appliance introduced in FIG. 1.
Figure 4:
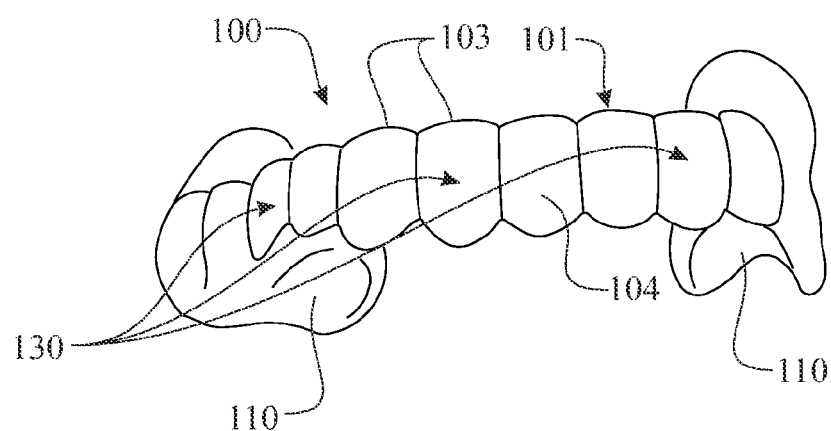
FIG. 4 presents a front perspective view of a prototype of the dental appliance introduced in FIG. 1.
Figure 5:
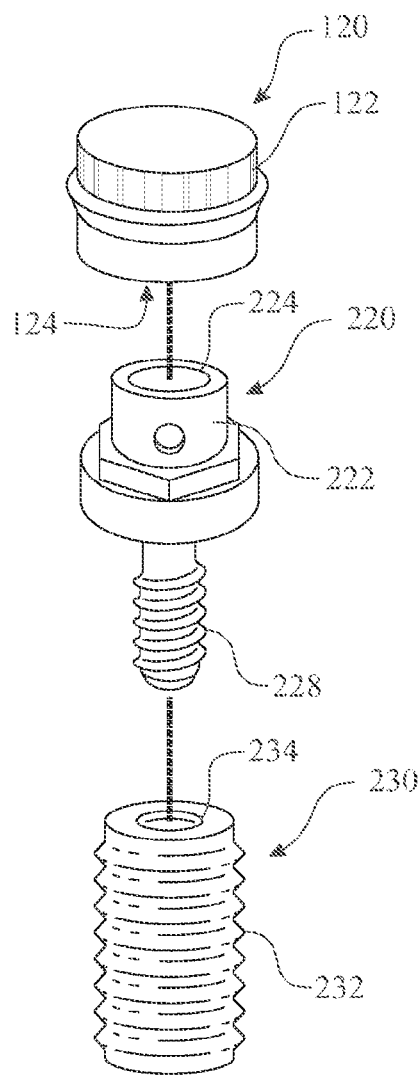
FIG. 5 presents an exploded isometric assembly view of an exemplary implanted appliance retention system.

As illustrated in FIGS. 1-4, the dental appliance 100 may include a teeth section 101 which is sized to snap over one or more of the patient's teeth 202 or cover one or more toothless sections 210 (FIGS. 1 and 2) of the patient's dentition. The dental appliance 100 can be described by a term of an exposed base portion 130, which refers to a visible portion thereof when the dental appliance 100 is in use and a term of a contact side 132, which refers to a contacting or attachment portion thereof, wherein the contact side 132 is used to attach the appliance 100 within the patient's mouth. As illustrated in FIGS. 3 and 4, a pair of toothless sections 110 may terminate the respective ends of the teeth section 101. The teeth section 101 may include at least one tooth receptacle 103 which is sized and configured to snap over a corresponding one of the patient's teeth 202. Each tooth receptacle 103 of the teeth section 101 may include an exterior wall member 104 and an interior wall member 106. A teeth engaging interface 102 (FIG. 3) is defined by and between the exterior wall member 104 and the interior wall member 106 of each tooth receptacle 103. When the dental appliance 100 is applied to the patient's teeth 202, the toothless sections 110 may contour to the gum line of the patient along missing teeth regions 210 which may exist in the patient's dentition as illustrated in FIGS. 1 and 2. The teeth engaging interface 102 receives the respective lower or upper teeth 202 and/or covers one or more missing teeth regions 210 of the patient's dentition. The exterior wall members 104 of the respective tooth receptacles 103 create a façade of at least a portion of the patient's teeth whereas the interior wall members 106 are positioned behind the teeth. Lower edges of the exterior wall member 104 and the interior wall member 106 may be positioned along the patient's gum line to create a seal and prevent food entrapment between the dental appliance 100 and the patient's teeth 202 during chewing of food.

One or more of the tooth receptacles 103 may simulate the appearance of one or more of the patient's teeth 202 in a missing tooth region 210 of the patient's dentition. In some embodiments of the dental appliance 100, the exterior wall members 104 of the respective tooth receptacles 103 may present a façade of an entire upper or lower set of the patient's teeth. In some embodiments, the dental appliance 100 may attach to a patient's upper or lower jaw in areas where the patient has a portion of natural teeth 202 and one or more missing teeth regions 210 from which one or more of the patient's natural teeth 202 are absent, as illustrated in FIGS. 12-15. Accordingly, the dental appliance 100 may include a section which attaches to the remaining portion of natural teeth 202 using a "snap-over" interface and a "snap-in" interface, as will be hereinafter described.

As illustrated in FIG. 3, the snap-over teeth engaging interface 102 may be formed between the exterior wall member 104 and the interior wall member 106 of the teeth section 101. The snap-over teeth engaging interface 102 may further include teeth abutment engaging features 109 that detachably engage teeth abutments 209 (FIGS. 1 and 10) between adjacent natural teeth 202 of the patient. The snap-over teeth engaging interface 102 may include or may alternatively utilize a securing feature (not illustrated) that detachably engages a tooth base 207 (FIG. 11) on each of the patient's remaining natural teeth 202 according to the knowledge of those skilled in the art.

In some applications of the dental appliance 100, gaps or spaces may exist as one or more missing teeth regions 210 (FIGS. 12 and 14) between some of the patient's teeth 202. Accordingly, as illustrated in FIGS. 5-9, removable retention components 120, 150 and fixed retention components 220, 250 (FIGS. 6 and 8) can be used to secure the dental appliance 100 to the missing teeth region or regions 210. The fixed retention components 220, 250 (FIGS. 6 and 8, respectively) may be permanently fixed to a patient's jaw typically as will be hereinafter described. The removable retention components 120, 150 are provided on the dental appliance 100 and may detachably engage the fixed retention components 220, 250, respectively. In some applications, the removable retention components 120, 150 may fixedly engage the fixed retention components 220, 250, respectively, according to the knowledge of those skilled in the art. Accordingly, the removable retention components 120, 150 and the respective fixed retention components 220, 250 may function as a retention system which additionally retains the dental appliance 100 on the dentition of the patient. The removable retention components 120, 150 and the fixed retention components 220, 250 may be formed of plastic, metal, or any other material which is suitable for fabrication of dental appliances and is consistent with the functional requirements of the dental appliance 100. Plastic versions of the removable retention components 120, 150 and the fixed retention components 220, 250 can be formed utilizing the flexibility of the material to aid in the detachable engagement design. Metallic versions of the removable retention components 120, 150 and the fixed retention components 220, 250 may include additional features for aiding in the detachable engagement process. Either of these applications, or any other utilization of the components, may be made according to the clinician's preference or choice.

Figure 6:
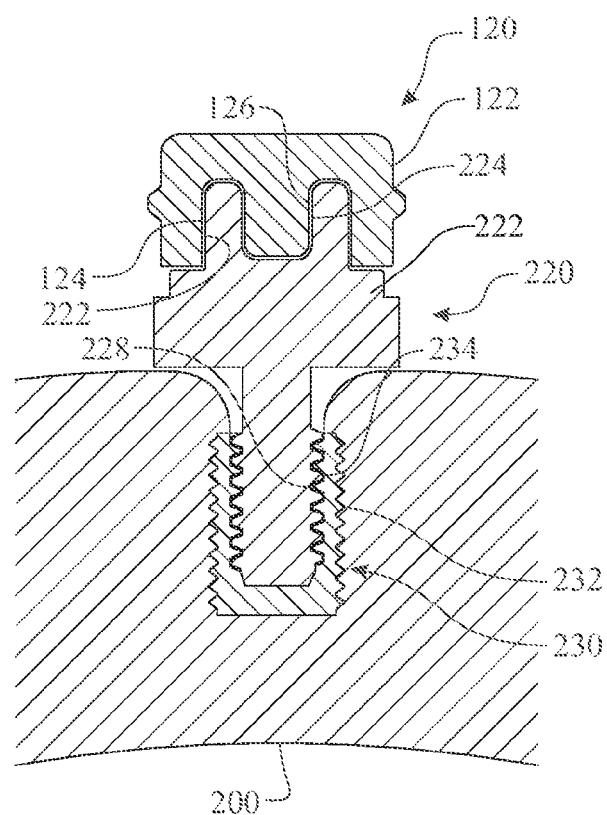
FIG. 6 presents an assembled sectioned elevation view of the implant-based appliance retention system introduced in FIG. 5, wherein a male component snaps into a female component.

As illustrated in FIG. 6, in areas of the patient's dentition in which a retained root 260 (FIG. 7) of a natural tooth 202 is no longer available or is considered to be inadequate for support or anchoring of the dental appliance 100, an implant 230 may be set into the patient's jaw 200 using a standard dental surgical procedure. A threaded implant anchor surface 232 may be provided on an exterior surface of the implant 230 to aid in securing and retaining the implant 230 within the patient's jaw 200. The fixed retention component 220 may be secured to the implant 230. Accordingly, a fixed retention anchor section 228 of the fixed retention component 220 may be inserted into a retentive component receptacle 234 of the implant 230. The fixed retention anchor section 228 may be threaded and rotationally received within a mating female threading formed within the retentive component receptacle 234. The removable retention component 120 may removably or fixedly engage a mating male interface 222 of the fixed retention component 220. The interface between the removable retention component 120 and the male interface 222 of the fixed retention component 220 may include a snap-type interface such as an over-denture attachment interface, for example and without limitation.

As illustrated in FIG. 8, in areas of the patient's dentition in which a retained root 260 is available and considered to be adequate for support or anchoring of the dental appliance 100, a fixed retention component 250 may be inserted into the retained root 260. The removable retention component 150 is provided on the dental appliance 100 and may engage the fixed retention component 250. A fixed retention anchor section 258 may be inserted and secured into a prepared site 264 formed in the retained root 260 using standard dental procedures. The fixed retention anchor section 258 may be commonly secured in the retained root 260 using a bonding media, a curing media, a cementing media, a screw friction retention or the like.

The removable retention component 120, 150 can be of any form factor, using any reasonably known detachably-engaging or fixedly-engaging retention interface device. Each removable retention component 120, 150 may have a female receptacle 124, 154 which receives a male interface 222, 252 on the fixed retention component 220, 250. The removable retention component 120, 150 can optionally include a retention member 126, 156, respectively, which engages a mating coupling cavity 224, 254, respectively, in the fixed retention component 220, 250 to increase a retention force. Alternatively, a small groove or undercut ring (not illustrated) can be formed within the interior surface of the removable retention component 120, 150, which groove or undercut ring mates with a mating ring or groove (not illustrated), respectively, formed on the mating male interface 222, 252 of the fixed retention component 220, 250. It is understood that other interfaces such as a magnetic interfaces and the like can be utilized to secure the removable retention components 120, 150 to the fixed retention components 220, 250, respectively. It is further understood that the structural characteristics of the removable retention components 120, 150 and the fixed retention components 220, 250 may be reversed. For example and without limitation, in some embodiments, the removable retention components 120, 150 may include male interfaces 222, 252 which engage companion female receptacles 124, 154 on the fixed retention components 220, 250.

Figure 9:
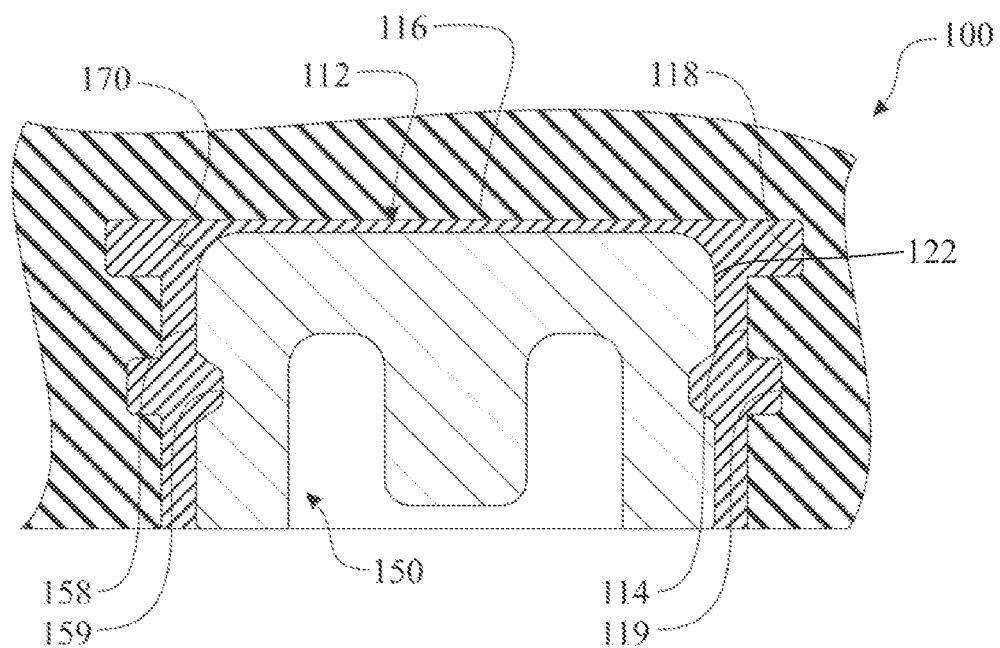
FIG. 9 presents a sectioned elevation view of the retention member assembled within a snap-in component receiving cavity formed in the dental appliance.
Figure 10:
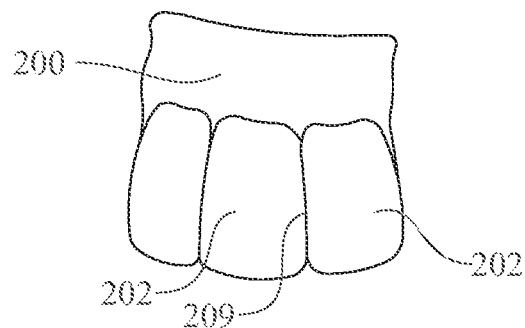
FIG. 10 presents a front elevation view of a section of a patient's remaining natural teeth available for use in conjunction with the "snap-over" retentive feature.
Figure 11:
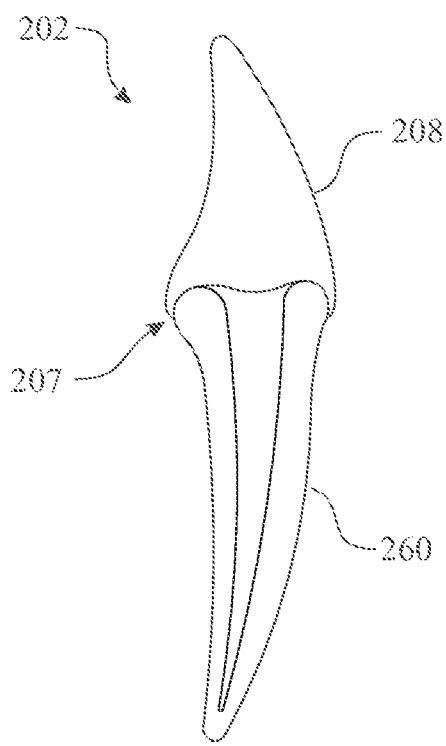
FIG. 11 presents a side sectioned view of a patient's tooth indicating available tooth surface contours that may provide the tooth-based appliance retentive feature.
Figure 12:
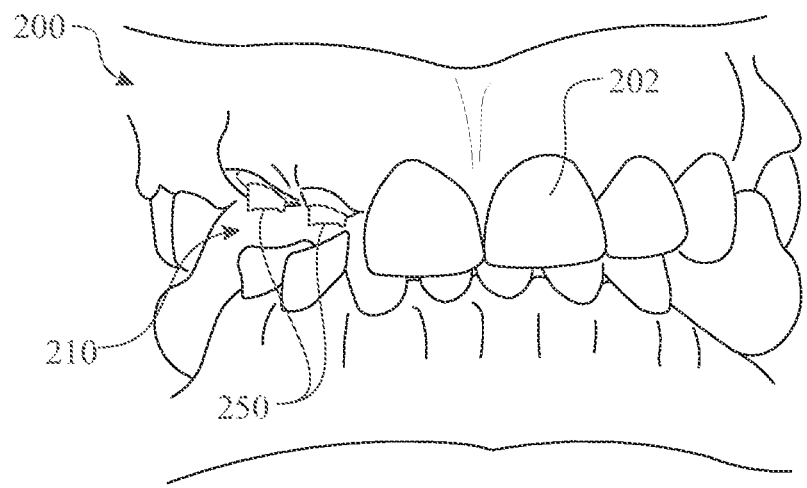
FIG. 12 presents a perspective rendering of a first patient's undesirable natural/existing smile due to the absence of several teeth, the rendering further illustrates the inclusion of several attachments for receiving the dental appliance.
Figure 13:
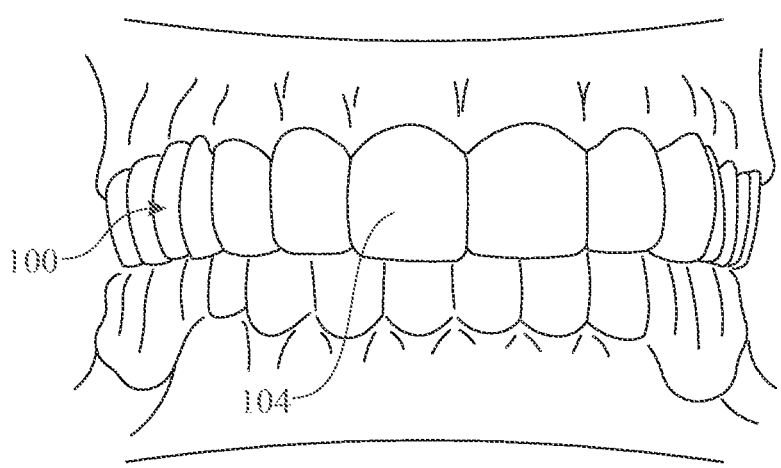
FIG. 13 presents a perspective rendering of the first patient's smile after insertion of the dental appliance illustrating the enhancement from the undesirable natural/existing smile presented in FIG. 12.
Figure 14:
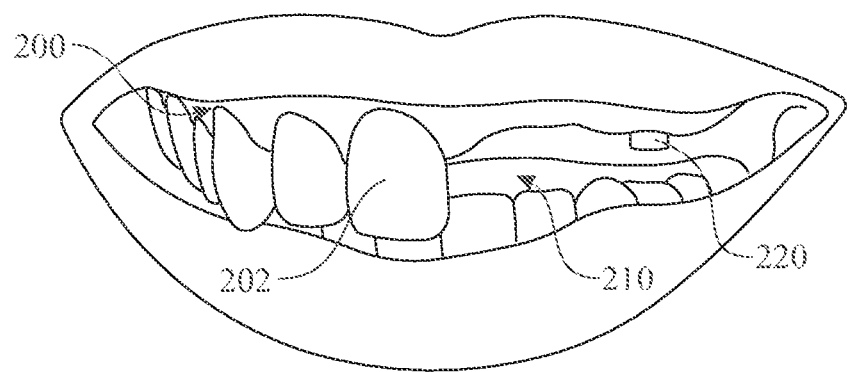
FIG. 14 presents a perspective rendering of a second patient's undesirable natural/existing smile, the rendering further illustrates the inclusion of an attachment in the patient's lateral edentulous area for retention of the dental appliance.
Figure 15:
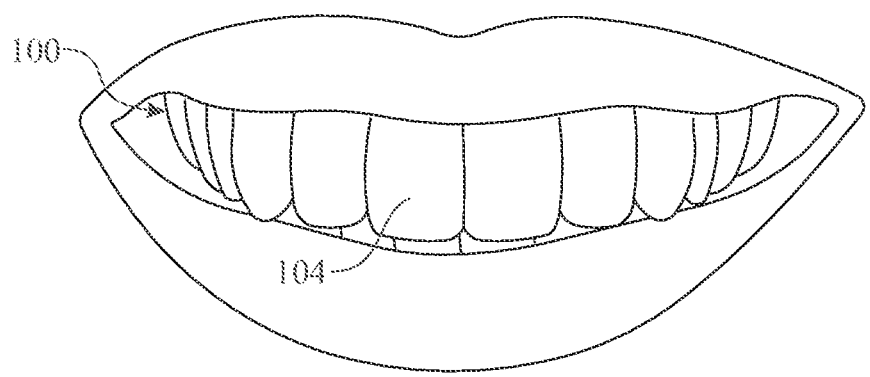
FIG. 15 presents a perspective rendering of the second patient's smile after insertion of the dental appliance illustrating the enhancement from the undesirable natural/existing smile presented in FIG. 14.

The removable retention components 120, 150 may be attached to the dental appliance 100 according to any suitable technique which is known by those skilled in the art. As illustrated in FIG. 9, in some embodiments, a snap-in component receiving cavity 112 may be provided in each toothless section 110 (FIG. 3) of the dental appliance 100. Each snap-in component receiving cavity 112 receives a corresponding removable retention component 120, 150. The snap-in component receiving cavity 112 may be shaped with a receiving cavity sidewall 114 which terminates at a receiving cavity end wall 116.

In some embodiments, mechanical undercut retention can be used to affix the removable retention component 120, 150 to the toothless section 110 or other component of the dental appliance 100. One or more undercuts (not illustrated) may be formed within the snap-in component receiving cavity 112 to aid in reliably securing the removable retention component 120, 150 in the component receiving cavity 112. Accordingly, as further illustrated in FIG. 9, a receiving cavity rear undercut 118 may be provided along the receiving cavity end wall 116 of the snap-in component receiving cavity 112. A receiving cavity central undercut 119 may additionally or alternatively be provided at any point along the receiving cavity sidewall 114. In some embodiments, multiple centrally-located undercuts 119 may be included in the receiving cavity sidewall 114 utilizing any suitable undercutting procedure. An adhesive compound 170 may be applied between a bonding surface 122, 152 of the removable retention component 120, 150 and the snap-in component receiving cavity 112 for mechanically securing the removable retention component 120, 150 within the snap-in component receiving cavity 112. The adhesive compound 170 may harden and conform to the shape of the snap-in component receiving cavity 112. The cured adhesive compound 170 may form within the undercut(s) 118, 119 (or similar) features to create a mechanical connection between the removable retention component 120, 150 and the dental appliance 100. Similarly, the removable retention component 120, 150 may include at least one exterior sidewall attachment groove 159 which may be formed within an exterior sidewall 158 of the removable retention component 120, 150, allowing the adhesive compound 170 to shape therein and form a mechanical connection.

The dental appliance 100 may be fabricated using a conventional laboratory process by initially taking a dental impression of the patient's dentition. The dental impression may be used to create a model, which may be used to fabricate the dental appliance 100 according to laboratory dental techniques and methods which are well-known by those skilled in the art. The dental appliance 100 provides the patient with a low-cost solution to achieving the appearance of a beautiful, natural smile. When the dental appliance 100 is installed on the patient's dentition, the patient's palate (not illustrated) may remain exposed as described above, maintaining the natural feel and function of the patient's palate. Therefore, the dental appliance 100 provides a relatively conservative solution for replacing or augmenting missing natural teeth 202 in those patients who may otherwise be vulnerable to the gag reflex when wearing conventional appliances. The dental appliance 100 provides a meaningful way to both replace or augment missing natural teeth 202 and enhance a patient's existing smile for upper and lower arches in circumstances in which the patient's health and/or limited resources would prohibit the patient from undergoing more involved dental procedures. The dental appliance 100 provides a possible alternative to a conventional removable partial appliance. Improved dental function and appearance imparted by the dental appliance 100 can positively affect both a patient's sense of well-being and overall self-esteem. A dental appliance 100 that can serve both of these purposes can be an asset for many patients. The dental appliance 100 can be utilized as a short-term or long-term functional and/or aesthetic solution for dental patients depending upon various conditions and considerations.

Figure 17:
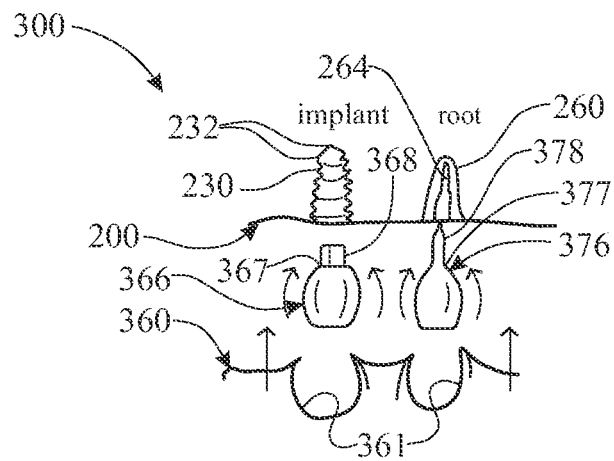
FIG. 17 presents a side sectional view illustrating attachment of a pair of abutments to an implant and a root, respectively, embedded in the jaw of a patient and more particularly illustrating attachment of the dental appliance to undercuts on the abutments.
Figure 18:
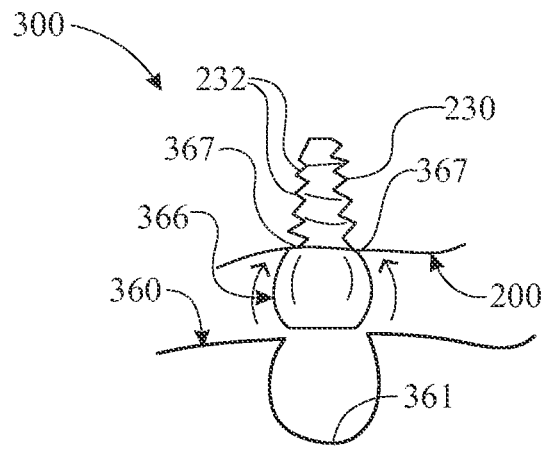
FIG. 18 presents a side sectional view illustrating attachment of the dental appliance to the undercuts on an abutment anchored in the patient's jaw via an implant.
Figure 19:
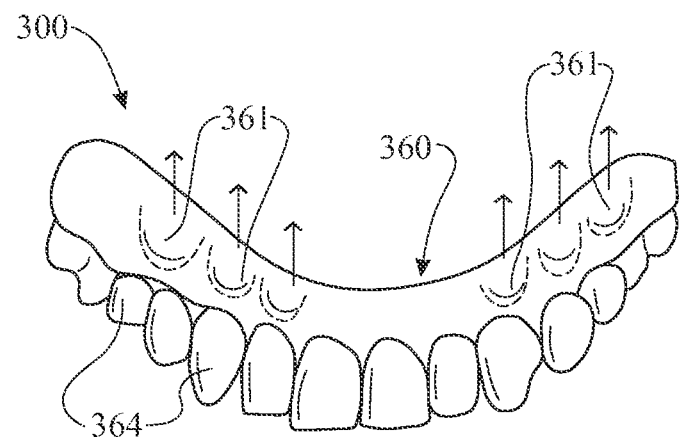
FIG. 19 presents a perspective view of the appliance with respective areas that would engage the undercut-designed abutment.

Referring next to FIGS. 16-19 of the drawings, an exemplary alternative use of a dental appliance 300 is generally indicated in FIG. 19. The dental appliance 300 may include an appliance base 360 which may conform to the contour of a patient's upper or lower dentition or jaw 200 (FIG. 26). Multiple abutment prepared surfaces 361 may be provided in the appliance base 360. Appliance teeth 364 may extend from the appliance base 360. The appliance teeth 364 present the appearance of a set of teeth on the patient's upper or lower jaw 200 upon application of the dental appliance 300 to the patient's jaw 200.

Multiple undercut-designed type of abutments 366, 376 may be attached to either a retained root 260 or an implant 230 in the patient's jaw 200 to facilitate attachment of the appliance base 360 to the jaw 200. Each abutment 366 for an implant 230, or abutment 376 for a tooth root 260, may be particularly effective in attaching the appliance base 360 to edentulous areas of the patient's jaw 200. Each abutment 366 may be adapted for attachment to an implant 230 in areas of the patient's jaw 200 which lack dentition that would otherwise provide sufficient support for attachment of the appliance base 360 to the patient's jaw 200. Each implant 230 may include implant threads 232 which are threaded into an implant opening (not illustrated) provided in the patients jaw 200 according to standard dental surgical techniques to secure or anchor the implant 230 in the patient's jaw 200. Each abutment 366, 376 may be generally spherical or knob-shaped and may include an abutment undercut 367, 377, respectively. An abutment shaft 368 may extend from the abutment 366. The abutment shaft 368 may be threadably inserted in a shaft opening (not illustrated) which is provided in the implant 230 to secure the abutment 366 to the implant 230.

Figure 16:
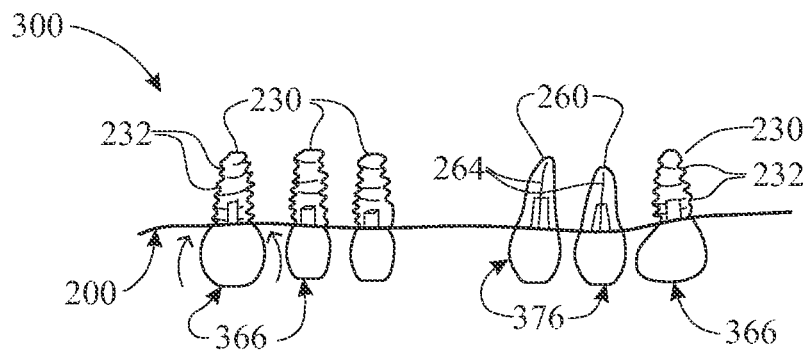
FIG. 16 presents a side view of multiple abutments anchored in a jaw of a patient via implants and tooth roots in attachment of an exemplary embodiment of the dental appliance to a patient's dentition.

As illustrated in FIGS. 16 and 17, each abutment 376 may be adapted for attachment to a retained root 260 in areas of the patient's jaw 200 which include teeth that would provide sufficient support for attachment of the appliance base 360 to the patient's jaw 200. The retained root 260 may include interior root threading 264 which may be formed according to standard dental surgical techniques. An abutment shaft 378 may extend from the abutment 376. The abutment shaft 378 may be designed to insert into the root threading 264 in the retained root 260 using a threaded or other attachment.

As illustrated in FIGS. 17 and 18, the appliance base 360 of the dental appliance 300 may be snapped over the abutments 366, 376 by inserting the abutments 366, 376 into the respective abutment openings 361 in the appliance base 360 in a snap-fit. Accordingly, the dental appliance 300 is attached to the abutments 366, 376 via the abutment undercuts 367, 377 on the abutments 366, 376. This feature enables the dental appliance 300 to be attached to partially or fully clinically edentulous areas in the upper or lower arches of the patient's jaw 200. Moreover, the abutment openings 361 in the appliance base 360 may be sized and configured to snap over prepared undercuts in existing teeth on the patient's jaw 200 in edentulous areas of the patient's jaw 200. This concept for effecting retention of the dental appliance 300 on the patient's jaw 200 can be combined with the conventional over-denture attachments or may be used as the sole mechanism for retention in clinically edentulous areas. Narrower-shaped abutments 366, 376 may be fabricated and used in the narrower areas (i.e., anterior portions) of the patient's mouth whereas wider abutments 366, 376 may be used in the wider areas (i.e., posterior portions) of the patient's mouth.

It will be appreciated by those skilled in the art that the abutments 366, 376 provide a similar type of attachment mechanism for the dental appliance 300 as that which can be attained using natural teeth. The undercut design is incorporated into the abutments 366, 376 and the dental appliance 300 can engage these undercuts 367, 377 in the same manner as it would otherwise engage a clinically natural tooth with its undercuts. In the narrower portions of the patient's jaw 200, the abutments 366, 376 may be shaped to resemble anterior teeth of the patient's dentition. In the wider portions of the patient's jaw 200, the abutments 366, 376 may be shaped to resemble posterior teeth of the patient's dentition.

Figure 20:
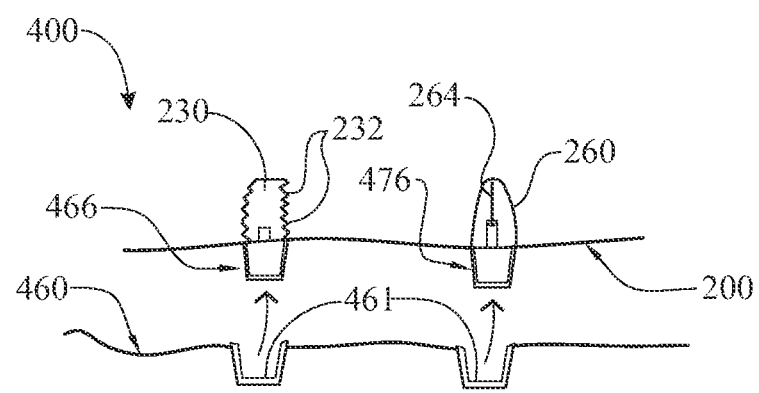
FIG. 20 presents a side sectional view illustrating a pair of abutments to an implant and a root, respectively, embedded in the jaw of a patient and more particularly illustrating attachment of the dental appliance to a friction-fit abutment interface.

Referring next to FIG. 20 of the drawings, an alternative illustrative embodiment of a dental appliance 400 is illustrated. The dental appliance 400 may include a pair of generally prepared-shaped abutments 466, 476 to an implant 230 and/or a root 260, respectively, embedded in the jaw 200 of a patient. An appliance base 460 may include multiple abutment openings 461 that correspond to the abutments 466, 476. Accordingly, the abutment openings 461 in the appliance base 460 may receive the abutments 466, 476, respectively, in a friction fit to detachably secure the appliance base 460 to the patient's jaw 200.

Since many modifications, variations, and changes in detail can be made to the described preferred embodiments of the invention, it is intended that all matters in the foregoing description and shown in the accompanying drawings be interpreted as illustrative and not in a limiting sense. For example, the use of the terms male/female as a means to explain/illustrate a sampled retentive system. Thus, the scope of the invention should be determined by the appended claims and their legal equivalence.

What is claimed is:

1. A dental appliance for application to a jaw of a dental patient for specific use as at least one of a denture, a prosthetic, and an aesthetic function, comprising:

an appliance base having a unitary construction formed as a "U" shape comprising an exposed base portion replicating at least a partial compliment of teeth for one of an upper jaw and a lower jaw of a dental patient and a contact side of said appliance formed to adapt to said one of patient's upper jaw and said patient's lower jaw, said contact side being segmented into a teeth receiving section and a toothless section, the "U" shape being defined by a front lower edge of each tooth of said at least partial compliment of teeth and a rear lower edge of each tooth of said at least partial compliment of teeth;

said teeth receiving section includes at least one tooth receptacle, each tooth receptacle comprising a recess extending inward from a contacting surface of said contact side of said appliance base, shaped for receiving and concealing a natural, generally healthy shaped tooth and a snap-over teeth engaging interface, where, when installed each tooth receptacle conceals each respective natural, generally healthy shaped tooth of a dental patient and said snap-over teeth engaging interface that having an surface conforming to the tooth including a tooth base section wherein the snap-over feature detachably engages with a tooth base of each respective natural, generally healthy shaped tooth of said dental patient to removably retain said appliance base in engagement with said one of an upper jaw and a lower jaw of a dental patient;

said toothless section includes at least one removable retention component carried by a patient toothless gum section contacting surface;

a mating fixed retention component for implanting into one of a patient's jaw and a patient's tooth root;

wherein each said removable retention component and said mating fixed retention component comprise detachable engaging attachment features to removable engaging with one another.

2. The dental appliance of claim 1 wherein said at least one mating fixed retention component further comprises a generally knob-shaped abutment.

3. The dental appliance of claim 1 further comprising at least one mating fixed retention component is adapted for implanting into said jaw of said dental patient.

4. The dental appliance of claim 1 further comprising at least one root implanted retention component adapted for implanting into a root of said dental patient.

5. A dental appliance for application to a jaw of a dental patient for specific use as at least one of a denture, a prosthetic, and an aesthetic function, comprising:

an appliance base having a unitary construction segmented into a contacting surface and an exposed teeth formation configured for one of an upper jaw and a lower jaw of a dental patient, the contact surface being concealed and the exposed teeth formation being visible when said appliance is installed in said jaw of said dental patient, wherein said exposed teeth formation replicates a plurality of teeth being arranged presenting a series of teeth as a group of adjacent and continuous teeth having a natural, generally healthy shaped appearance, the appliance base being formed in a "U" shape which is defined by a front lower edge of each tooth of said at least partial compliment of teeth and a rear lower edge of each tooth of said at least partial compliment of teeth;

at least one tooth receptacle formed within said contacting surface, each tooth receptacle comprising a recess extending inward and shaped for receiving and concealing each respective natural, generally healthy shaped tooth, and a snap-over teeth engaging interface, where, when installed each tooth receptacle conceals each respective natural, generally healthy shaped tooth of said dental patient and said snap-over teeth engaging interface having an surface conforming to the tooth including a tooth base section wherein the snap-over feature detachably engages with a tooth base of each respective natural, generally healthy shaped tooth to removably retain said appliance base in engagement with said one of an upper jaw and a lower jaw of a dental patient;

at least one appliance engaging interface component carried by said contacting surface of said appliance base; and at least one implanted retention member, wherein when installed, each said appliance engaging interface component detachably engages with said respective implanted retention member.

6. The dental appliance of claim 5 wherein said at least one tooth receptacle comprises a plurality of adjacent tooth receptacles.

7. The dental appliance of claim 6 further comprising a plurality of teeth abutment engaging features between adjacent ones of said plurality of adjacent tooth receptacles.

8. The dental appliance of claim 5 further comprising at least one toothless section formed along a portion of said contacting surface of said appliance base, wherein said toothless section is shaped to conform to each edentulous areas of the patient's mouth.

9. The dental appliance of claim 8 wherein said at least one toothless section comprises a pair of toothless sections formed along a contacting surface segment proximate each respective end of said appliance base.

10. The dental appliance of claim 9 wherein said at least one appliance engaging interface component is carried by at least one of said pair of toothless sections.

11. The dental appliance of claim 10 wherein said at least one appliance engaging interface component comprises a pair of appliance engaging interface component carried by said pair of toothless sections, respectively.

12. The dental appliance of claim 5 wherein said at least one tooth receptacle comprises an exterior wall member, an interior wall member spaced-apart from said exterior wall member and a teeth engaging interface between said exterior wall member and said interior wall member.

13. A dental appliance for application to a jaw of a dental patient for specific use as at least one of a denture, a prosthetic, and an aesthetic function, comprising:
an appliance base having a unitary construction segmented into a contacting surface and an exposed teeth formation configured for one of an upper jaw and a lower jaw of a dental patient, the contact surface being concealed and the exposed teeth formation being visible when said appliance is installed in said jaw of said dental patient, wherein said exposed teeth formation replicates a plurality of teeth being arranged presenting a series of teeth as a group of adjacent and continuous teeth having a natural, generally healthy shaped appearance, the appliance base being formed in a "U" shape which is defined by a front lower edge of each tooth of said at least partial compliment of teeth and a rear lower edge of each tooth of said at least partial compliment of teeth;
a plurality of tooth receptacles formed within said contacting surface, each tooth receptacle comprising a recess extending inward and shaped for receiving and concealing each respective natural, generally healthy shaped tooth, and
a snap-over teeth engaging interface, where, when installed each tooth receptacle conceals each respective natural, generally healthy shaped tooth of said dental patient and said snap-over teeth engaging interface having an surface conforming to the tooth including a tooth base section wherein the snap-over feature detachably engages with a tooth base of each respective natural, generally healthy shaped tooth to removably retain said appliance base in engagement with said one of an upper jaw and a lower jaw of a dental patient;
at least one appliance engaging interface component carried by said contacting surface of said appliance base, said at least one appliance engaging interface component having a first one of a male interface and a female receptacle;
at least one implanted retention component, wherein each implanted retention component is designed to detachably engage with said respective appliance engaging interface component, and
said implanted retention component having a second one of a male interface and a female receptacle and engaging said first one of a male interface and a female receptacle.

14. The dental appliance of claim 13 wherein said at least one appliance engaging interface component comprises a female receptacle and said at least one implanted retention component comprises a male interface.

15. The dental appliance of claim 13, said implanted retention component is a jaw implanted retention component adapted for implanting into said jaw of said dental patient.

16. The dental appliance of claim 13, said implanted retention component is a root implanted retention component adapted for implanting into a root of said dental patient.

17. The dental appliance of claim 13, further comprising a plurality of teeth abutment engaging features between adjacent ones of said plurality of adjacent tooth receptacles.

18. The dental appliance of claim 13, further comprising at least one toothless section formed along a portion of said contacting surface of said appliance base, wherein said toothless section is shaped to conform to each edentulous areas of the patient's mouth.

19. The dental appliance of claim 18 wherein said at least one toothless section comprises a pair of toothless sections formed along a contacting surface segment proximate each at respective end of said appliance base.

20. The dental appliance of claim 19 wherein said at least one appliance engaging interface component is carried by at least one of said pair of toothless sections.

21. The dental appliance of claim 20 wherein said at least one appliance engaging interface component comprises a pair of removable retention components carried by said pair of toothless sections, respectively.

22. The dental appliance of claim 13 wherein each of said plurality of adjacent tooth receptacles comprises an exterior wall member, an interior wall member spaced-apart from said exterior wall member and a teeth engaging interface between said exterior wall member and said interior wall member.

* * * * *

UNITED STATES PATENT AND TRADEMARK OFFICE
CERTIFICATE OF CORRECTION

Page 1 of 4

PATENT NO. : 8,764,445 B1
APPLICATION NO. : 13/209705
DATED : July 1, 2014
INVENTOR(S) : DeLuca It is certified that error appears in the above-identified patent and that said Letters Patent is hereby corrected as shown below:

On the title page, item [56], insert between the reference identified as 7,234,940 B1 to Weissman and 7,758,346 to Letcher as follows:

-- 7,357,637 B2 * 4/2008 Liechtung ............................................ 433/167 --

On title page 2, item [56], column 1, line 4, should read as follows:

-- NON-PATENT LITERATURE --

-- Preferred Family Dental, "Understanding Implants & Snap-On Smile", 15 Nov 09 - 2 Oct 10, Internet Archive https://web.archive.org/web/20101002060945/http://www.pfdent.com/Mini%20Implants.understandingimplants.html --

In the Claims

Column 9, line 39, Claim 1, delete "1. A dental appliance for application to a jaw ..."" and ending "... with one another." in column 10, line 9, and insert:

-- 1. A dental appliance for application to a jaw of a dental patient for specific use as at least one of a denture, a prosthetic, and an aesthetic function, comprising:
    an appliance base having a unitary construction formed as a "U" shape comprising an exposed base portion replicating at least a partial compliment of teeth for one of an upper jaw and a lower jaw of the dental patient and a contact side of said appliance formed to adapt to said one of patient's upper jaw and said patient's lower jaw, said contact side being segmented into a teeth receiving section and a toothless section, the "U" shape being defined by a front lower edge of each tooth of said at least partial compliment of teeth and a rear lower edge of each tooth of said at least partial compliment of teeth;

Signed and Sealed this
Twenty-seventh Day of January, 2015

Michelle K. Lee
*Deputy Director of the United States Patent and Trademark Office*

CERTIFICATE OF CORRECTION (continued)
U.S. Pat. No. 8,764,445 B1 said teeth receiving section includes at least one tooth receptacle, each tooth receptacle comprising a recess extending inward from a contacting surface of said contact side of said appliance base, shaped for receiving and concealing a natural, generally healthy shaped tooth and a snap-over teeth engaging interface, where, when installed each tooth receptacle conceals each respective natural, generally healthy shaped tooth of the dental patient and said snap-over teeth engaging interface having a surface conforming to the tooth and including a tooth base section having a snap-over feature, wherein the snap-over feature detachably secures with a tooth base of each respective natural, generally healthy shaped tooth of said dental patient to removably retain said appliance base in engagement with said one of an upper jaw and a lower jaw of the dental patient; said toothless section includes at least one removable retention component carried by a patient toothless gum section contacting surface;

a mating fixed retention component for implanting into one of a patient's jaw and a patient's tooth root; wherein each said removable retention component and said mating fixed retention component comprise detachable engaging attachment features to removable engaging with one another. --

Column 10, line 10, Claim 2, delete "2. The dental appliance of claim 1 wherein said at least one ..." and ending "... knob-shaped abutment." in column 10, line 12, and insert:

-- 2. The dental appliance of claim 1 wherein said mating fixed retention component further comprises a generally knob-shaped abutment. --

Column 10, line 13, Claim 3, delete "3. The dental appliance of claim 1 further comprising at ..." and ending "... knob-shaped abutment." in column 10, line 15, and insert:

-- 3. The dental appliance of claim 1 wherein said mating fixed retention component is adapted for implanting into said jaw of said dental patient. --

Column 10, line 16, Claim 4, delete "4. The dental appliance of claim 1 further comprising at ..." and ending "... knob-shaped abutment." in column 10, and insert:

-- 4. The dental appliance of claim 1 wherein said mating fixed retention component is adapted for implanting into a root of said dental patient. --

Column 10, line 20, Claim 5, delete "5. A dental appliance for application to a jaw of a dental ..." and ending "... implanted retention member." in column 10, line 59, and insert:

-- 5. A dental appliance for application to a jaw of a dental patient for specific use as at least one of a denture, a prosthetic, and an aesthetic function, comprising:

an appliance base having a unitary construction segmented into a contacting surface and an exposed teeth formation configured for one of an upper jaw and a lower jaw of the dental patient, the contacting surface being concealed and the exposed teeth formation being visible when said appliance is installed in said jaw of said dental patient, wherein said exposed teeth formation replicates a plurality of teeth being arranged presenting a series of teeth presenting as a group of adjacent and continuous teeth having a natural, generally healthy shaped appearance, the appliance base being CERTIFICATE OF CORRECTION (continued)
U.S. Pat. No. 8,764,445 B1 formed in a "U" shape which is defined by a front lower edge of each tooth of said plurality of teeth and a rear lower edge of each tooth of said plurality of teeth; and
wherein said contacting surface includes a teeth receiving section and at least one toothless section;
    at least one tooth receptacle formed within the teeth receiving section of said contacting surface, each tooth receptacle comprising a recess extending inward from the contacting surface and shaped for receiving and concealing each respective natural, generally healthy shaped tooth, and a snap-over teeth engaging interface, where, when installed each tooth receptacle conceals each respective natural, generally healthy shaped tooth of said dental patient and said snap-over teeth engaging interface having an surface conforming to the tooth and including a tooth base section having a snap-over feature, wherein the snap-over feature detachably engages with a tooth base of each respective natural, generally healthy shaped tooth to removably retain said appliance base in engagement with said one of an upper jaw and a lower jaw of the dental patient; said at least one toothless section includes at least one removable appliance engaging interface component carried by said contacting surface of said appliance base; and
    at least one implanted retention member adapted for implanting into one of a patient's jaw and a patient's tooth root, wherein when installed, said at least one removable appliance engaging interface component detachably engages with said at least one respective implanted retention member. --

Column 10, line 66, Claim 8, delete "8. The dental appliance of claim 5 further comprising ..."" and ending "... the patient's mouth." in column 11, line 3, and insert:

-- 8. The dental appliance of claim 5 wherein said at least one toothless section is shaped to conform to each edentulous areas of the patient's jaw. --

Column 11, line 20, Claim 13, delete "13. A dental appliance for application to a jaw of a dental ..."" and ending "... tsaid first one of a male interface and a female receptacle." in column 12, line 14, and insert:

-- 13. A dental appliance for application to a jaw of a dental patient for specific use as at least one of a denture, a prosthetic, and an aesthetic function, comprising:
    an appliance base having a unitary construction segmented into a contacting surface and an exposed teeth formation configured for one of an upper jaw and a lower jaw of the dental patient, the contact surface being concealed and the exposed teeth formation being visible when said appliance is installed in said jaw of said dental patient, wherein said exposed teeth formation replicates a plurality of teeth being arranged presenting a series of teeth presenting as a group of adjacent and continuous teeth having a natural, generally healthy shaped appearance, the appliance base being formed in a "U" shape which is defined by a front lower edge of each tooth of said plurality of teeth and a rear lower edge of each tooth of said plurality of teeth; and wherein said contacting surface includes a teeth receiving section and at least one toothless section;
    a plurality of tooth receptacles formed within the teeth receiving section of said contacting surface, each tooth receptacle comprising a recess extending inward from said contacting surface and shaped for receiving and concealing each respective natural, generally healthy shaped tooth of said dental patient, and
a snap-over teeth engaging interface, where, when installed each tooth receptacle conceals each respective natural, generally healthy shaped tooth of said dental patient and said snap-over teeth engaging interface having a surface conforming to the tooth including a tooth base section having a snap-over feature detachably engages with a tooth base of each respective natural, generally healthy shaped tooth to removably retain said appliance base in engagement with said one of an upper jaw and a lower jaw of the dental patient;

said at least one toothless section includes at least one appliance engaging interface component carried by said contacting surface of said appliance base, said at least one appliance engaging interface component having a first one of a male interface and a female receptacle;

at least one implanted retention component adapted for implanting into one of a patient's jaw and a patient's tooth root, wherein each implanted retention component is designed to detachably engage with said respective appliance engaging interface component, and said implanted retention component having a second one of a male interface and a female receptacle and engaging said first one of a male interface and a female receptacle. --

Column 12, line 28, Claim 18, delete "18. The dental appliance of claim 13 further comprising at ..."" and ending "... the patient's mouth." in column 12, line 32, and insert:

-- 18. The dental appliance of claim 13 wherein said at least one toothless section is shaped to conform to each edentulous areas of the patient's jaw. --

Column 12, line 44, Claim 22, delete "22. The dental appliance of claim 13 wherein each of said ..."" and ending "... said exterior wall member and said interior wall member." in column 12, line 48, and insert:

-- 22. The dental appliance of claim 13 wherein each of said plurality of tooth receptacles comprises an exterior wall member, an interior wall member spaced-apart from said exterior wall member and a teeth engaging interface between said exterior wall member and said interior wall member. --